(12) United States Patent
Cho

(10) Patent No.: US 7,511,167 B2
(45) Date of Patent: Mar. 31, 2009

(54) TWO-PHOTON DYES FOR REAL-TIME IMAGING OF LIPID RAFTS

(75) Inventor: Bong-Rae Cho, Seoul (KR)

(73) Assignee: Korea University Industry and Academy Cooperation Foundation, Seoul (KR)

(*) Notice: Subject to any disclaimer, the term of this patent is extended or adjusted under 35 U.S.C. 154(b) by 0 days.

(21) Appl. No.: 11/824,588

(22) Filed: Jun. 29, 2007

(65) Prior Publication Data
US 2008/0071106 A1    Mar. 20, 2008

(30) Foreign Application Priority Data
Jun. 29, 2006   (KR) .................. 10-2006-0059329
Jun. 28, 2007   (KR) .................. 10-2007-0064801
Jun. 28, 2007   (KR) .................. 10-2007-0064803

(51) Int. Cl.
*C07F 9/02*     (2006.01)
*C07C 229/00*   (2006.01)

(52) U.S. Cl. ........................... 558/169; 562/452

(58) Field of Classification Search ............. None
See application file for complete search history.

(56) References Cited

OTHER PUBLICATIONS

Kim et al, ChemBioChem, A Two-photon Fluorescent Probe for Lipid Raft Imaging: C-laurdan, 2007, 8(5), pp. 553-559.*

* cited by examiner

*Primary Examiner*—Paul A Zucker
(74) *Attorney, Agent, or Firm*—Edwards Angell Palmer & Dodge LLP; Peter F. Corless

(57) ABSTRACT

Two-photon dyes for real-time imaging of lipid rafts are provided. The two-photon dyes emit fluorescence with high intensity in the environments of cell membranes and can be used to clearly discriminate the hydrophobic and hydrophilic domains of the cell membranes. Therefore, the use of the two-photon dyes enables satisfactory imaging of actual lipid raft domains. In addition, since the two-photon dyes show no cytotoxicity, they can be suitably used in bioimaging applications, for example, real-time imaging of lipid rafts over a long period of time.

7 Claims, 11 Drawing Sheets
(10 of 11 Drawing Sheet(s) Filed in Color)

(a)

(b)

(c)

TWO-PHOTON DYES FOR REAL-TIME IMAGING OF LIPID RAFTS

CROSS-REFERENCE TO RELATED APPLICATION

The present application claims, under 35 U.S.C. §119, the benefit of Korean Patent Application Nos. 10-2006-0059329 filed Jun. 29, 2006, 10-2007-0064801 filed Jun. 28, 2007, and 10-2007-0064803 filed Jun. 28, 2007, the entire contents of which are hereby incorporated by reference.

BACKGROUND OF THE INVENTION

1. Technical Field

The present invention relates to two-photon dyes for real-time imaging of lipid rafts. More specifically, the present invention relates to two-photon dyes that are highly soluble in water, show no cytotoxicity and emit two-photon fluorescence with high intensity, thus being suitable for use in real-time imaging of lipid rafts.

2. Background Art

In recent years, lipid rafts have been proposed to be cell organelles involved in signal transduction. Research on the mechanisms of the incidence of diseases through lipid rafts is now actively underway. Lipid rafts refer to rafts floating on a 'sea of phospholipids.' Specifically, lipid rafts are plasma membranes having rigid compartments composed of glycosphingolipids and cholesterol and floating on a sea of glycerophospholipids. The rigid compartments accommodate many cellular molecules to mediate different cellular procedures, such as signal transduction, and are separated from one another. In the case where signaling molecules are randomly oriented in fluid plasma membranes, the efficiency and speed of the cellular signal transduction procedure are considerably lowered. To render the signal transduction procedure efficient, media are required that allow the signaling molecules to gather at particular locations and organize the signaling molecules. Such media are known as lipid rafts. Lipid rafts contain receptors for various factors, such as EGFs, PDGFs, insulin, IGFs, VEGFs and TNFs, and numerous signaling molecules. Accordingly, lipid rafts can be defined as centers of signal transduction procedure. Lipid rafts are also known to be intimately associated with the mechanisms of the incidence of diseases, e.g., bovine spongiform encephalopathy (BSE), dementia, cancers and bacterial diseases.

For a better understanding of signal transduction, bovine spongiform encephalopathy (BSE), dementia, cancers and the like, much research has been conducted on lipid rafts. Lipid rafts have a diameter not larger than 100 nm, making it impossible to observe their real shape using optical microscopes. Attempts using atomic force microscopes (AFMs) have been made to observe the shape of lipid rafts. The topology of living cells is complex because proteins and glycoconjugates other than lipid components are attached to the cell surface, thus making it impossible to identify the presence of lipid rafts in the living cells. Further, fluorescence microscopy has been employed to observe the shape of lipid raft proteins in living cells by attaching green fluorescent proteins (GFPs) to the lipid raft proteins. The presence of lipid rafts in lipid raft proteins leads to the expression of a dotted pattern of the proteins. However, no lipid raft protein has heretofore remained a dotted pattern. The presence or absence of lipid rafts in living cells has become a controversial issue.

Under these circumstances, attempts have recently been made to obtain molecular images of lipid rafts using fluorescent markers. A fluorescent marker that is most widely used in molecular imaging of lipid rafts is Laurdan, which was developed by Professor Weber 20 years ago and is currently available from Molecular Probes Inc. This substance can be helpful in explaining the behaviors of liquid ordered phases and liquid disordered phases of model membranes, and is thus utilized in the model study of cell membranes. Recent studies have been conducted to demonstrate the presence of lipid rafts in cell membranes by staining the cells with Laurdan (PNAS, 1996, 93, 11443), but have proved to provide irreproducible experimental results.

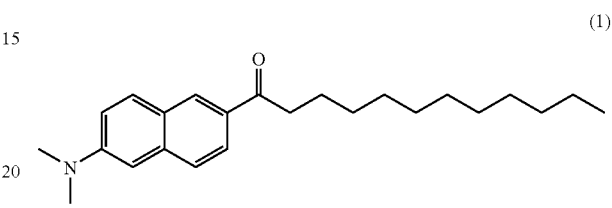

(1)

Laurdan represented by Formula 1, which was developed as a one-photon fluorescent dye, absorbs photons of about 365 nm to reach the excited state. Laurdan in the excited state returns to the ground state, emitting fluorescence of specific wavelengths. The wavelength of the fluorescence emitted varies depending on the polarity of solvents used to dissolve Laurdan (Weber G, et al., *Biochemistry* 18:3075-3078 (1979)). Laurdan is currently used as a two-photon fluorescent dye for cellular imaging.

In 1932, Maria Goeppert-Mayer predicted a phenomenon in which two photons are spontaneously absorbed (*Ann, Phys.* 9(1931) 273), but this two-photon excitation had not been practically utilized until strong laser sources were developed. Two-photon excitation is referred to as a phenomenon in which two photons are simultaneously absorbed in the same luminophore having a sufficiently high photon density per unit volume and time by irradiation with a strong light source. The absorbed energy is the same as the sum of the energies of the two photons and the possibility of two-photon excitation is dependent on the square of the photon density. Accordingly, the absorption of two photons is a secondary non-linear optical phenomenon. The photons in the excited state transit to the ground state, emitting energy as fluorescence corresponding to the bandgap energy. This energy emission is called 'two-photon fluorescence.' It should be understood that the emitted photonic energy is greater than the photonic energy of an irradiation source. Substances emitting fluorescence by two-photon excitation are commonly termed 'two-photon dyes.' Such two-photon dyes may be excited by means of a light source capable of providing photonic energy corresponding to the bandgap energy. This excitation is referred to as 'one-photon excitation.' A fluorescence emission spectrum obtained by two-photon excitation has the same spectral properties as that by one-photon excitation.

A first characteristic of two-photon excitation is that the excitation occurs only near the limited three-dimensional regions of light irradiators, and therefore, fluorescence emission obtained by the excitation is localized in three-dimensional space, resulting in a minimization of background fluorescence. A second characteristic of two-photon excitation is that the wavelength of the irradiated light is different from that of the emitted fluorescence. Particularly, the two-photon excitation is useful in observing small-volume samples because the excitation volume is very small.

Based on the above-mentioned characteristics, two-photon microscopy capable of inducing two-photon excitation by irradiation of light in the near-infrared region is currently in the spotlight in bioimaging applications. The reason for this is due to the following advantages: i) little damage of biomolecules by the irradiation of near-infrared light, which enables the application of two-photon microscopy to living cells; ii) large penetration depth of near-infrared light; and iii) minimized tissue auto-fluorescence.

Two-photon dyes used for two-photon microscopy must satisfy the following requirements: i) the two-photon dyes must have a large two-photon cross section ($\delta_{TPA}$) in the near-infrared region; ii) the two-photon dyes must be dissolved to some extent in water, iii) the two-photon dyes must be highly photostable; and iv) the two-photon dyes must bind well to living cells.

Laurdan may be incorporated within cell membranes because it structurally has a hydrophobic tail. Laurdan present in cell membranes may be an important determinant of the cell membrane fluidity. Fluorescence resonance energy transfer (FRET) is a method for identifying the presence of lipid rafts. Cell membranes of eukaryotic cells are known to have fluid phospholipid domains and rigid lipid raft domains. The phospholipid domains are in a relatively hydrophilic environment through which water freely passes due to the presence of unsaturated fatty acids therein, whereas the lipid raft domains composed of glycolipids and cholesterol are less fluid and highly rigid due to the presence of saturated fatty acids and cholesterol therein and are thus in a relatively hydrophobic environment through which water does not easily pass. Laurdan emits fluorescence ranging from 470 to 530 nm in the phospholipid domains in a hydrophilic environment and emits fluorescence ranging from 400 to 460 nm in the lipid raft domains in a hydrophobic environment. Based on these fluorescence emission characteristics, Laurdan has been used in visualizing lipid rafts in cell membranes (Gaus et al., PNAS, 100, 15554, 2003; Gaus et al., JCB, 171, 121, 2005). However, Laurdan is barely soluble in water such that it produces a precipitate emitting fluorescence of 450 nm, which is confused with the emission wavelengths in the lipid raft domains. Therefore, Laurdan has a limitation in the visualization of lipid rafts, does not precisely reflect the polarity of solvents, and suffers from a problem in that the intensity of fluorescence emitted in intracellular environments, whose major component is water, is not sufficiently high. Within cell membranes in a mixed state of phospholipids and lipid rafts, Laurdan preferentially binds to the rigid membrane domains. In conclusion, Laurdan is not suitable for use in the discrimination of images of rigid membrane domains from those of fluid membrane domains.

SUMMARY OF THE INVENTION

Thus, it is an object of the present invention to provide two-photon dyes whose polarity is optimized to equally control the interactions with hydrophilic domains and hydrophobic domains of cell membranes, and that emit fluorescence with high intensity in intracellular environments and are used to clearly discriminate rigid domains from fluid domains in the cell membranes to achieve imaging of the domains, thus being suitable for use in the visualization and real-time imaging of lipid rafts.

In order to accomplish the above object of the present invention, there are provided two-photon dyes for real-time imaging of lipid rafts, represented by Formula 2:

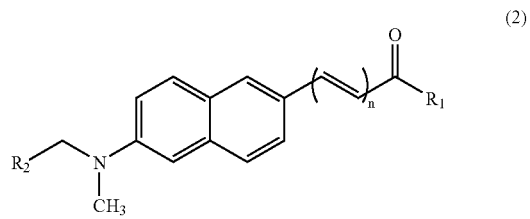

wherein $R_1$ $C_5$-$C_{17}$ alkyl group,
n is 0 or 1, and
$R_2$ is —COOH, —CH$_2$SO$_3$Na or

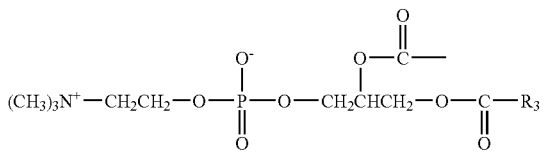

($R_3$ is a $C_5$-$C_{17}$ alkyl group).

BRIEF DESCRIPTION OF THE DRAWINGS

The patent or application file contains at least one drawing executed in color. Copies of this patent or patent application publication with color drawing(s) will be provided by the Office upon request and payment of necessary fee.

The above and other objects, features and other advantages of the present invention will be more clearly understood from the following detailed description taken in conjunction with the accompanying drawing, in which.

DETAILED DESCRIPTIONS

Figure 1:
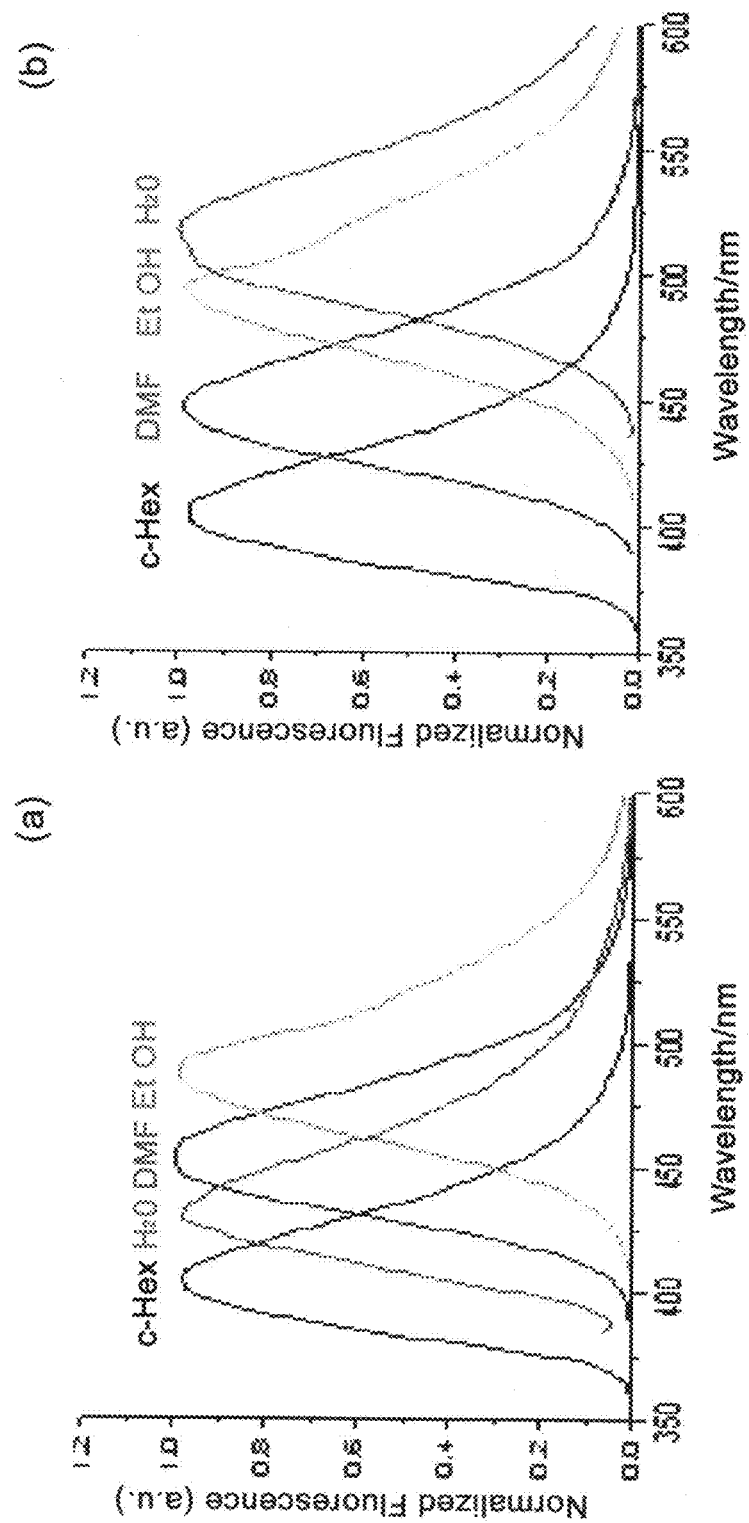
FIGS. 1a and 1b show changes in the one-photon emission wavelength of two-photon dyes prepared in Comparative Example 1 (FIG. 1a) and Example 1 (FIG. 1b) according to the polarity of solvents used.

The present invention provides two-photon dyes that readily stain cell membranes due to their good interactions with lipids, emit fluorescence with high intensity in the environments of the cell membranes, whose major component is water, emit fluorescence of 430-470 nm in a highly hydrophobic environment (solvents, liposomes or GUVs) and fluorescence of 470-530 nm in a hydrophilic environment (solvents, liposomes or GUVs) to enable clear discrimination between the hydrophobic and hydrophilic environments, so that lipid rafts present in the cell membranes can be imaged in real time, and show no cytotoxicity so as to achieve real-time imaging of the lipid rafts over a long period of time.

The two-photon dyes of the present invention are represented by Formula 2:

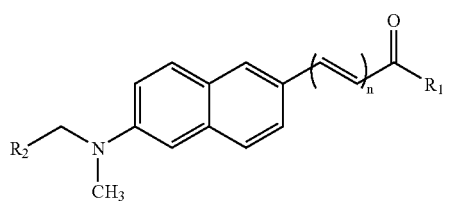

(2)

wherein $R_1$ is $C_5$-$C_{17}$ alkyl group,
n is 0 or 1, and
$R_2$ is —COOH, —CH$_2$SO$_3$Na or

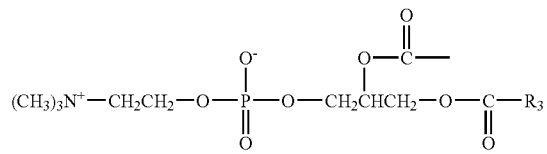

($R_3$ is a $C_5$-$C_{17}$ alkyl group).

In an embodiment of the present invention, the compounds of Formula 2 include the following compounds (3):

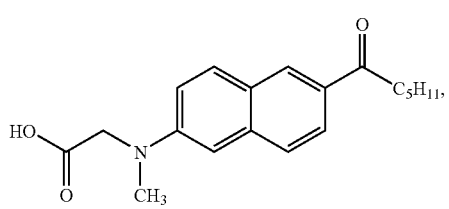

(3)

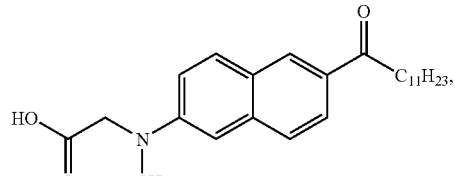

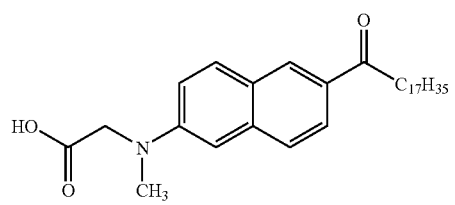

In a further embodiment of the present invention, the compounds of Formula 2 include the compound represented by Formula 4:

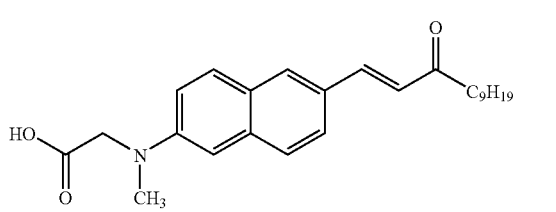

(4)

In another embodiment of the present invention, the compounds of Formula 2 include the following compounds (5):

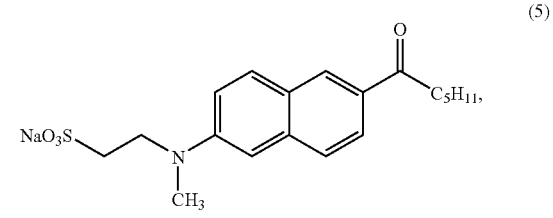

(5)

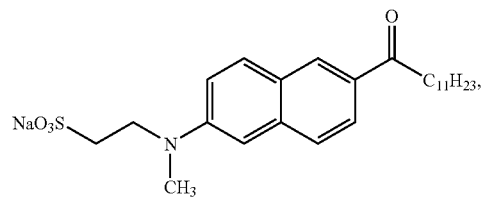

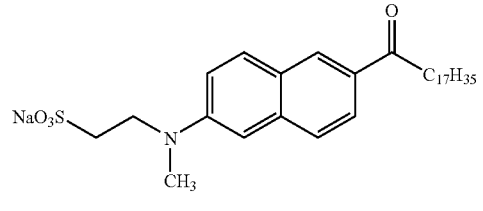

In another embodiment of the present invention, the compounds of Formula 2 include the following compounds (6):

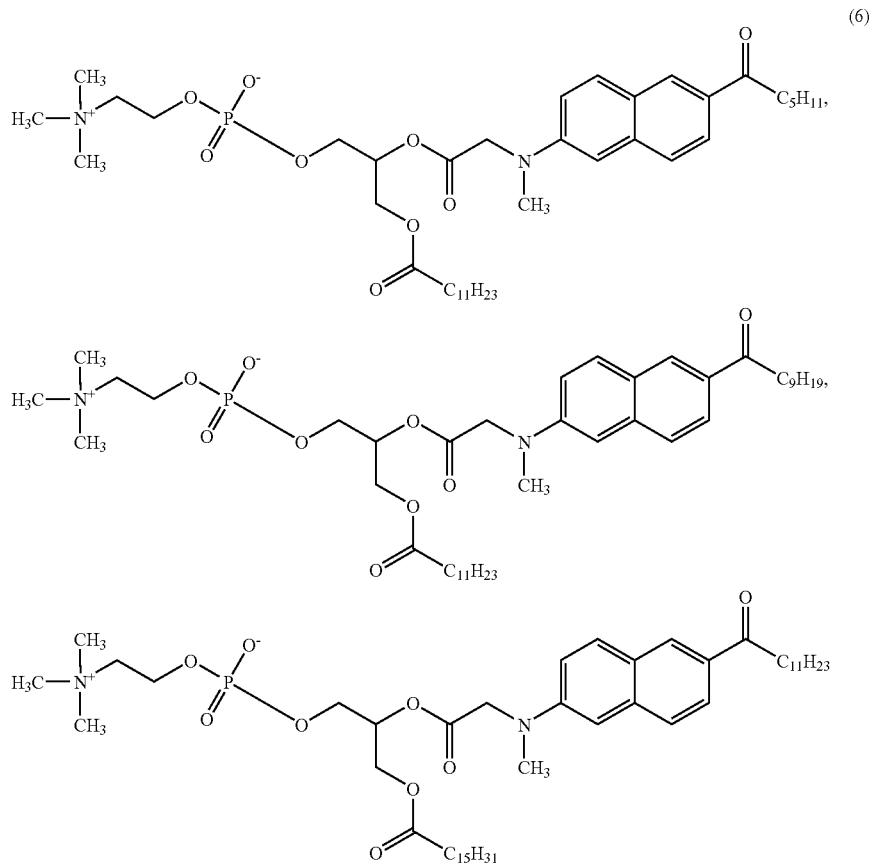

In another embodiment of the present invention, the two-photon dyes may have a two-photon absorption efficiency not lower than 20 GM ($10^{-50}$ cm$^4$s/photon) in living cells, may be two-photon excited by a light source at 750-1,000 nm, and may emit fluorescence ranging from 400 to 700 nm.

In a preferred embodiment of the present invention, the two-photon dyes may have a two-photon absorption efficiency not lower than 150 GM, and may emit fluorescence of 430-470 nm in a highly hydrophobic environment (solvents, liposomes or GUVs) and fluorescence of 470-530 nm in a hydrophilic environment (solvents, liposomes or GUVs).

The two-photon dyes of the present invention are highly soluble in water due to the presence of the polar group ($R_2$). Since the two-photon dyes of the present invention exhibit good interactions between lipids within cell membranes, they can be used to homogeneously stain the cell membranes and obtain brighter images. In addition, the two-photon dyes of the present invention absorb near-infrared light to emit fluorescence, causing no damage to cells and less photobleaching. Therefore, the use of the two-photon dyes is very advantageous in obtaining real-time images over a long period of time. Various polar groups, such as carbonyl (TPD1), sulfonyl (TPD2) and phosphatidylcholine (TPD3), may be introduced into $R_2$ to render the shapes of the two-photon dyes similar to those of fatty acids and phospholipids of actual cells.

$R_1$, a hydrophobic moiety, serves to incorporate the two-photon dyes into cell membranes. $R_1$ is preferably a $C_5$-$C_{17}$ alkyl group. When the number of carbon atoms in $R_1$ is smaller than 5, the hydrophobicity of the two-photon dyes is negligible. When the number of carbon atoms in $R_1$ exceeds 17, the water solubility of the two-photon dyes drops dramatically to cause the formation of a precipitate, which is the problem encountered in Laurdan, thus making the two-photon dyes unsuitable as probes.

The reason why $R_3$ is preferably a $C_5$-$C_{17}$ alkyl group is because the hydrophilic and hydrophobic positions of cell membranes can be selectively stained according to the length of the hydrophobic carbon atoms. This selective staining enables imaging of numerous cellular functions.

The two-photon dyes have a two-photon absorption efficiency not lower than 20 GM in living cells, are excited by a light source at 750-1,000 nm, and emit fluorescence ranging from 400 to 700 nm. More preferably, the two-photon dyes have a two-photon absorption efficiency not lower than 150 GM.

As mentioned above, Laurdan, a representative two-photon dye, emits fluorescence of 470-530 nm in phospholipids in a hydrophilic environment and fluorescence of 400-460 nm in lipid rafts in a hydrophobic environment. Based on these characteristics, Laurdan has been used to visualize lipid rafts in cell membranes. Laurdan is scarcely soluble in water such that it produces a precipitate, which emits fluorescence of 450 nm even in a hydrophilic environment. As a result, Laurdan has a limitation in the visualization of lipid rafts. In contrast, the two-photon dyes of the present invention are highly soluble in water, leaving no precipitate at concentrations suitable for use as markers. In addition, the two-photon dyes of the present invention emit fluorescence of 430-470 nm in a highly hydrophobic environment (solvents, liposomes or GUVs) and fluorescence of 470-530 nm in a hydrophilic environment (solvents, liposomes or GUVs) to enable clear discrimination between the hydrophobic and hydrophilic environments by the emitted fluorescence wavelengths. Furthermore, the two-photon dyes of the present invention are very useful in identifying a change in the fluidity of plasma membranes and dynamic movement of lipid rafts in cells undergoing various stresses (e.g., thermal impact, hypoxia and hypertonic solution impact).

As described below, the two-photon dyes of the present invention show symmetrical distributions of generalized polarization (GP) values in hydrophilic and hydrophobic environments of cell membranes, and are uniformly distributed in hydrophilic and hydrophobic domains within the cell membranes, thus enabling precise observation of lipid rafts.

On the other hand, when n is 1 in Formula 2, the electron donor is more distant from the electron acceptor, resulting in an increased dipole moment of the two-photon dyes. This increased dipole moment leads to a smooth charge transfer in a polar solvent or a hydrophilic environment and results in a decreased energy gap between the ground state and the excited state in the electronic energy levels of the two-photon dyes. The decreased energy gap increases the proportion of energy that is not transferred into fluorescence and is instead decayed into other forms, leading to a decrease in fluorescence quantum yield and fluorescence lifetime. As a result, the intensity of fluorescence is greatly reduced. In this case, since the two-photon dyes are strongly sensitive to the polarity of cell membranes, they emit fluorescence only in hydrophobic domains and fluorescence with extremely low intensity in hydrophilic domains. Accordingly, the two-photon dyes have an advantage in that lipid rafts can be observed through images obtained by direct fluorescence without the need to convert the GP values, which will be explained below, into additional GP images. The use of GP images enables two-dimensional observation of lipid rafts, whereas the use of direct images obtained by direct fluorescence enables three-dimensional observation of lipid rafts.

Hereinafter, the present invention will be explained in more detail with reference to the preferred examples. However, these examples are not intended to limit the present invention.

EXAMPLES

Example 1

1-(1): Preparation of 6-dodecanoyl-N-methyl-2-naphthylamine

MeNH$_2$.HCl (11.0 g, 0.13 mol) was added to a mixture of 2-hydroxy-6-dodecanoylnaphthalene (8.0 g, 25 mmol), Na$_2$S$_2$O$_5$ (12 g, 61 mmol), NaOH (5.2 g, 0.13 mol) and water (100 ml) in a high-pressure tube. The resulting mixture was stirred at 140° C. for 48 hours, followed by filtration to collect a solid. The solid was sufficiently washed with water and recrystallized from CH$_2$Cl$_2$-EtOH to give the title compound (5.6 g, yield: 67%).

$^1$H-NMR (300 MHz, CDCl$_3$): δ 8.31 (s, 1H), 7.94 (dd, J=9.0, 3.0 Hz, 1H), 7.72 (d, J=9.0 Hz, 1H), 7.64 (d, J=9.0 Hz, 1H), 6.91 (dd, J=9.0, 3.0 Hz, 1H), 6.77 (s, 1H), 3.97 (br s, 1H), 3.03 (t, J=7.5 Hz, 2H), 2.97 (s, 3H), 1.77 (quin, J=7.5 Hz, 2H), 1.26 (m, 16H), 0.88 (t, J=7.5 Hz, 3H); $^{13}$C-NMR (75 MHz, CDCl$_3$): ε 200.59, 149.30, 138.23, 130.91, 130.87, 130.08, 126.22, 126.19, 125.05, 118.60, 103.28, 38.64, 32.15, 29.88, 29.86, 29.78, 29.77, 29.76, 29.74, 29.58, 25.09, 22.92, 14.36.

1-(2): Preparation of TPD1

A mixture of 6-dodecanoyl-N-methyl-2-naphthylamine (3.0 g, 8.8 mmol) prepared in Example 1-(1), methyl bromoacetate (2.0 g, 13 mmol), Na$_2$HPO$_4$ (1.9 g, 13 mmol) and NaI (0.5 g, 3.5 mmol) was stirred under a nitrogen atmosphere at 80° C. for 18 hours. The reaction mixture was extracted with ethyl acetate, sufficiently washed with brine, and recrystallized from ethanol to obtain an intermediate as a yellow solid. A mixture of the intermediate (2.0 g, 4.9 mmol) and KOH (0.70 g, 12 mmol) in ethanol (50 ml) was stirred for 5 hours. After the resulting solution was diluted with ice-water (100 ml), concentrated hydrochloric acid was added thereto at 5° C. or lower until pH=3, followed by filtration to collect a precipitate. The precipitate was sufficiently washed with distilled water and recrystallized from chloroform-petroleum ether to give TPD1 (1.5 g, yield: 79%) as a white solid.

$^1$H-NMR (300 MHz, DMSO d$_6$): δ 12.70 (br s, 1H), 8.43 (s, 1H), 7.89 (d, J=9.0 Hz, 1H), 7.80 (d, J=9.0 Hz, 1H), 7.66 (d, J=9.0 Hz, 1H), 7.20 (d, J=9.0 Hz, 1H), 6.92 (s, 1H), 4.26 (s, 2H), 3.09 (s, 3H), 3.03 (t, J=7.5 Hz, 2H), 1.61 (quin, J=7.5 Hz, 2H), 1.22 (m, 16H), 0.83 (t, J=7.5 Hz, 3H); $^{13}$C-NMR (75 MHz, DMSO d$_6$): δ 199.91, 172.44, 149.83, 137.75, 131.30, 130.71, 130.46, 126.66, 125.44, 124.69, 116.70, 105.56, 100.29, 39.75, 38.17, 31.99, 29.72, 29.70, 29.68, 29.65, 29.46, 29.41, 24.92, 22.80, 14.66.

Example 2

Preparation of TPD2

A mixture of 6-dodecanoyl-N-methyl-2-naphthylamine (3.0 g, 8.8 mmol) prepared in Example 1-(1), BrCH$_2$CH$_2$SO$_3$Na (2.1 g, 10.0 mmol) and proton-sponge (2.2 g, 10.3 mmol) was stirred in DMF (50 ml) under a nitrogen atmosphere at 150° C. for 12 hours. The reaction mixture was extracted with water and dichloromethane, sufficiently washed with brine, and evaporated to remove the solvents. The residue was purified by column chromatography on silica gel using methanol/ethyl acetate (1:5) and recrystallized from chloroform to give TPD2 (1.8 g, yield: 44%).

$^1$H-NMR (300 MHz, CDCl$_3$): δ 8.42 (s, 1H), 7.90 (d, J=9.0 Hz, 1H), 7.89 (dd, J=9.0, 3.0 Hz, 1H), 7.62 (d, J=9.0 Hz, 1H), 7.20 (dd, J=9.0, 3.0 Hz, 1H), 6.90 (s, 1H), 3.71 (t, J=7.5 Hz, 2H), 3.08 (t, J=7.5 Hz, 2H), 3.01 (s, 3H), 2.68 (t, J=7.5 Hz, 2H), 1.61 (quin, J=7.5 Hz, 2H), 1.26 (m, 16H), 0.83 (t, J=7.5 Hz, 3H).

Example 3

Preparation of TPD3

A mixture of TPD1 (1.6 g, 4.0 mmol) prepared in Example 1-(2), the compound of Formula 7 (1.0 g, 2.0 mmol), DCC (2.4 g, 11.6 mmol) and dimethylaminopyridine (DMAP) (0.24 g, 2.0 mmol) was stirred in chloroform (50 ml) under a nitrogen atmosphere for 96 hours.

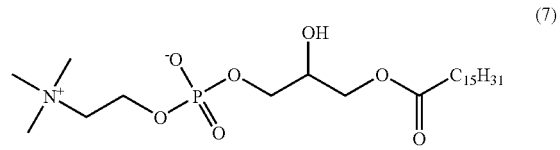

(7)

Then, the reaction mixture was evaporated to remove the solvent. Purification by column chromatography on silica gel using chloroform/methanol/water (18:9:1) gave TPD3 (2.2 g, yield: 63%).

$^1$H-NMR (600 MHz, CDCl$_3$): δ 8.27 (s, 1H), 7.88 (d, J=9.0 Hz, 1H), 7.77 (d, J=9.0 Hz, 1H), 7.62 (d, J=9.0 Hz, 1H), 7.08 (d, J=9.0 Hz, 1H), 6.85 (s, 1H), 5.23 (br m, 1H), 4.39 (d, J=9.5 Hz, 1H), 4.26 (d, J=18 Hz, 1H), 4.18 (d, J=18 Hz, 1H), 4.16 (s,

2H), 4.06 (dd, J=12 Hz, 6.6 Hz, 1H), 3.94 (br s, 2H), 3.57 (br s, 2H), 3.14 (br s, 12H), 2.99 (t, J=7.2 Hz, 2H), 2.08 (t, J=7.8 Hz, 2H), 1.72 (m, 2H), 1.43 (m, 2H), 1.38-1.14 (m, 40H), 0.85 (t, J=7.0 Hz, 6H).

Example 4

4-(1): Preparation of 6-methylamino-2-naphthonitrile

A solution of 6-bromo-N-methyl-2-naphthylamine (2.0 g, 8.5 mmol) in pyridine (50 ml) was added to copper (I) cyanide (1.1 g, 12.3 mmol). The mixture was stirred at 220° C. for 4 hours. The reaction mixture was allowed to cool to room temperature, extracted with dichloromethane, washed with an aqueous solution of hethylene diamine (10 vol %), and purified by column chromatography using hexane/ethyl acetate (4:1) as an eluting solvent to give the title compound (1.1 g, yield: 71%).

$^1$H NMR (400 MHz, CDCl$_3$): δ 8.01 (d, 1H, J=2 Hz), 7.63 (d, 1H, J=9 Hz), 7.62 (d, 1H, J=9 Hz), 7.46 (dd, 1H, J=9, J=2 Hz), 6.93 (dd, 1H, J=9, J=2 Hz), 6.73 (d, 1H, J=2 Hz), 4.23 (br s, 1H), 2.97 (s, 3H); $^{13}$C NMR (100 MHz, CDCl$_3$): δ (Ppm) 149.5, 137.4, 134.0, 129.7, 127.3, 126.9, 126.2, 119.4, 104.4, 103.2, 100.2, 30.6.

4-(2): Preparation of 6-formyl-N-methyl-2-naphthylamine

A solution of 6-methylamino-2-naphthonitrile (0.84 g, 4.6 mmol) prepared above in toluene (50 ml) was mixed with diisobutylaluminum hydride (9 ml, 1.0M (in toluene)) under a nitrogen atmosphere at −70° C. The mixture was stirred at −78° C. for 30 minutes and at room temperature for 4 hours. The mixture was added to a saturated solution of ammonium chloride, and then an aqueous solution of sulfuric acid was added thereto. The reaction mixture was extracted with ether, washed with brine, dried over MgSO$_4$, and concentrated to give the title compound (0.76 g, yield: 89%).

$^1$H NMR (300 MHz, CDCl$_3$): δ 10.01 (s, 1H), 8.13 (s, 1H), 7.83 (d, 1H, J=9 Hz), 7.74 (d, 1H, J=9 Hz), 7.66 (d, 1H, J=9 Hz), 6.92 (d, 1H, J=9 Hz), 6.78 (s, 1H), 4.25 (br s, 1H), 2.97 (s, 3H); $^{13}$C NMR (100 MHz, CDCl$_3$): δ (ppm) 192.1, 149.9, 139.3, 134.9, 131.0, 130.9, 126.9, 126.2, 124.0, 118.7, 103.5, 30.6.

4-(3): Preparation of TPD4

2-Undecanone (0.72 g, 4.2 mmol) was added to a solution of 6-formyl-N-methyl-2-naphthylamine (0.51 g, 2.8 mmol) prepared above, an aqueous NaOH (5 ml, 1M) and 60 ml of ethanol. The mixture was stirred for 24 hours, followed by filtration to collect a precipitate. The precipitate was washed with methanol and distilled water to obtain 0.58 g (yield: 61%) of an intermediate. Then, a solution of the intermediate (0.32 g, 0.95 mmol), proton-sponge (0.24 g, 1.1 mmol) and t-butyl bromoacetate (0.37 g, 1.9 mmol) in MeCN was stirred under a nitrogen atmosphere for 8 hours. Subsequently, the reaction mixture was extracted with ethyl acetate, washed with brine, dried over MgSO$_4$, concentrated and recrystallized from ethanol to give TPD4 (0.35 g, yield: 82%).

$^1$H NMR (400 MHz, CDCl$_3$): δ 7.80 (d, 1H, J=2 Hz), 7.71 (d, 1H, J=9 Hz), 7.67 (d, 1H, J=16 Hz), 7.61 (d, 1H, J=9 Hz), 7.58 (dd, 1H, J=9, J=2 Hz), 7.06 (dd, 1H, J=9, J=2Hz), 6.86 (d, 1H, J=2 Hz), 6.77 (d, 1H, J=16Hz), 4.09 (s, 2H), 3.19 (s, 3H), 2.67 (t, 2H, J=7 Hz), 1.69 (quin, 2H, J=7 Hz), 1.42 (s, 9H), 1.28 (m, 12H), 0.88 (t, 3H, J=7 Hz); $^{13}$C NMR (100 MHz, CDCl$_3$): δ (ppm) 201.1, 170.0, 148.4, 143.4, 136.4, 130.6, 130.0, 128.6, 127.2, 126.7, 124.6, 124.3, 116.0, 106.5, 82.1, 55.6, 41.1, 40.1, 32.1, 29.8, 29.7, 29.6, 29.5, 29.3, 24.9, 22.9, 14.3.

Comparative Example 1

1-(1): Preparation of 2-methoxy-6-dodecanoylnaphthalene

2-Methoxynaphthalene (30.1 g, 0.19 mol) was added to a solution of aluminum chloride (32.9 g, 0.25 mol) in anhydrous nitrobenzene under a nitrogen atmosphere. To the mixture was slowly added dropwise lauryl chloride (41.6 g, 0.19 mol) at 10-13° C. over 15 minutes. The resulting mixture was stirred at 5° C. for 2 hours and at room temperature for 12 hours. The reaction mixture was poured into 300 ml of 3M HCl at 0° C., extracted with chloroform, and sufficiently washed with brine. The solvents were removed by evaporation under reduced pressure. The residue was dissolved in chloroform and washed with 0.1M NaOH. The mixture was evaporated to remove the chloroform, followed by recrystallization from ethanol to give the title compound (41.5 g, yield: 64.2%).

$^1$H-NMR (300 MHz, CDCl$_3$): δ 8.40 (s, 1H), 8.01 (dd, J=9.0, 3.0 Hz, 1H), 7.86 (d, J=9.0 Hz, 1H), 7.77 (d, J=9.0 Hz, 1H), 7.20 (dd, J=9.0, 3.0 Hz, 1H), 7.16 (s, 1H), 3.95 (s, 3H), 3.06 (t, J=7.5 Hz, 2H), 1.78 (quin, J=7.5 Hz, 2H), 1.26 (m, 16H), 0.87 (t, J=7.5 Hz, 3H).

1-(2) Preparation of Laurdan

Li (0.5 g, 70 mmol) was added to HMPA (20 ml) and benzene (30 ml), and then dimethylamine (3.5 g, 78 mmol) was added dropwise thereto. The mixture was violently stirred for one hour. To the resulting mixture was added 2-methoxy-6-dodecanoylnaphthalene (7.3 g, 22 mmol) prepared in Comparative Example 1-(1) all at one time. The mixture was stirred at room temperature for 5 hours. The reaction mixture was poured into ice-water, extracted with ether, evaporated to remove the solvents, and recrystallized from ethanol to give Laurdan (5.1 g, yield: 66%).

$^1$H-NMR (300 MHz, CDCl$_3$): 8.31 (s, 1H), 7.94 (dd, J=9.0, 3.0 Hz, 1H), 7.81 (d, J=9.0 Hz, 1H), 7.64 (d, J=9.0 Hz, 1H), 7.17 (dd, J=9.0, 3.0 Hz, 1H), 6.87 (s, 1H), 3.11 (s, 6H), 3.04 (t, J=7.5 Hz, 2H), 1.78 (t, J=7.5 Hz, 2H), 1.37-1.27 (m, 16H), 0.89 (t, J=7.5 Hz, 3H).

Test Example 1

Reflection Tests of Polarity of Solvents

Time-resolved fluorescence (TRF) spectra of the two-photon dyes prepared in Comparative Example 1 and Example 1 were measured to examine changes in the one-photon fluorescence wavelength of the dyes according to the polarity of solvents. The results are shown in FIGS. 1a and 1b. In this test, hexane, DMF, ethanol and water were used as solvents. The polarity of the solvents increases in the order: hexane<DMF<ethanol<water. Referring to FIG. 1a, the maximum fluorescence wavelength of the two-photon dye (hereinafter, referred to as 'Laurdan') prepared in Comparative Example 1 increased as the polarity of the solvents increased. However, the maximum fluorescence wavelength of Laurdan in water with the highest polarity decreased (i.e. blue-shifted) and the wavelength width of Laurdan in water was broadened. These results are because Laurdan was substantially insoluble in water to produce aggregates. Since Laurdan has a long hydrocarbon tail, the dye molecules surrounded by the adjacent dye molecules were placed in a hydrophobic environment, and as a result, a blue shift was observed. That is, Laurdan present in water did not reflect the hydrophilic environment, and instead, emitted light of 400-460 nm, which corresponds to the wavelength range of fluorescence emitted in the hydrophobic environment. From these observations, it can be concluded that Laurdan is not suitable for use in real-time imaging of lipid rafts. In contrast, as the polarity of the solvents increased, the maximum fluorescence wavelength of the two-photon dye (hereinafter, referred to as 'TPD1') prepared in Example 1 increased (FIG. 1b), demonstrating that TPD1 sufficiently reflected the solvent polarity. As is apparent from these results, TPD1 can be used to clearly discriminate light-emitting domains depending on the difference in the polarity of cell membranes.

Figure 2:
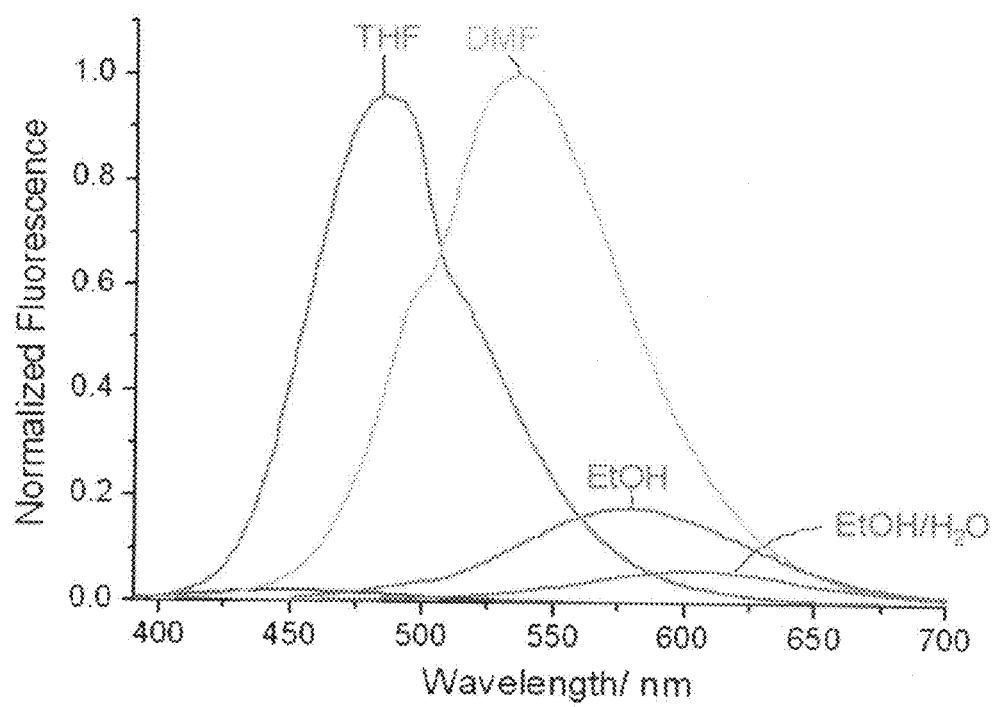
FIG. 2 shows changes in the one-photon emission wavelength of a two-photon dye prepared in Example 4 according to the polarity of solvents used.

On the other hand, time-resolved fluorescence (TRF) spectra of the two-photon dye (TPD4) prepared in Example 4 were measured to examine changes in the one-photon fluorescence wavelength of the dye according to the polarity of solvents. The results are shown in FIG. 2. In this test, THF, DMF, ethanol and ethanol/water were used as solvents. The polarity of the solvents increases in the order: THF<DMF<ethanol<ethanol/water. Referring to FIG. 2, unlike TPD1 and Laurdan, the fluorescence intensity of TPD4 was reduced drastically as the polarity of the solvents increased. As mentioned previously, the reason for this is because the fluorescence quantum yield and fluorescence lifetime of TPD4 in a hydrophilic environment were decreased drastically. Therefore, lipid rafts can be directly observed due to the difference in fluorescence intensity.

Test Example 2

Spectroscopic Measurements

The two-photon dyes prepared in Example 1 and Comparative Example 1 were dissolved in four solvents (hexane, DMF, ethanol and water), respectively. The one-photon maximum absorption wavelength ($\lambda_{max}$), one-photon maximum emission wavelength ($\lambda^{fl}_{max}$), two-photon maximum absorption wavelength ($\lambda^{(2)}_{max}$), quantum yield ($\Phi$) and two-photon absorption efficiency ($\delta_{max}$) of the solutions were measured, and the results are shown in Table 1. The absorption spectra were measured on a Hewlett-Packard 8453 diode array spectrophotometer. The fluorescence spectra were obtained with an Aminco Bowman series 2 luminescence spectrometer. The two-photon absorption efficiency means a maximum value of a two-photon cross section ($\delta_{TPA}$). The two-photon cross section can be calculated by the following equation 1:

$$\delta = \frac{S_s \Phi_r \phi_r c_r}{S_r \Phi_s \phi_s c_s} \delta_r \qquad (1)$$

wherein the subscripts s and r represent sample and reference molecules, respectively, $\delta$ represents the two-photon cross section, S represents the strength of signals collected by a CCD detector, $\Phi$ represents the fluorescence quantum efficiency, $\phi$ represents the total fluorescence collection efficiency of an experimental system, c represents the number density of the molecules within each of the solutions, and $\delta_r$ represents the two-photon cross section of reference molecules.

The data shown in Table 1 demonstrate that the quantum yields (fluorescence quantum efficiency) of the two-photon dyes prepared in Example 1 and Comparative Example 1 in DMF and ethanol are considerably high. The quantum yields of the two-photon dyes prepared in Comparative Example 1 and Example 1 in water were decreased to 1/100 and 1/4 of those of the dyes in ethanol, respectively. The reason why the quantum yield of Laurdan in water was sharply decreased is due to quenching arising from the occurrence of precipitation. This sharp decrease in quantum yield brings about a decrease in fluorescence intensity. On the other hand, the dye prepared in Example 1 showed a two-photon absorption efficiency of a minimum of 153 GM and a maximum of 323 GM, which correspond to about three to six times those of the dye prepared in Comparative Example 1. These results suggest that the two-photon dye prepared in Example 1 is more efficient than Laurdan.

Test Example 3

Reflection Tests of Polarity of Liposomes

Figure 3:
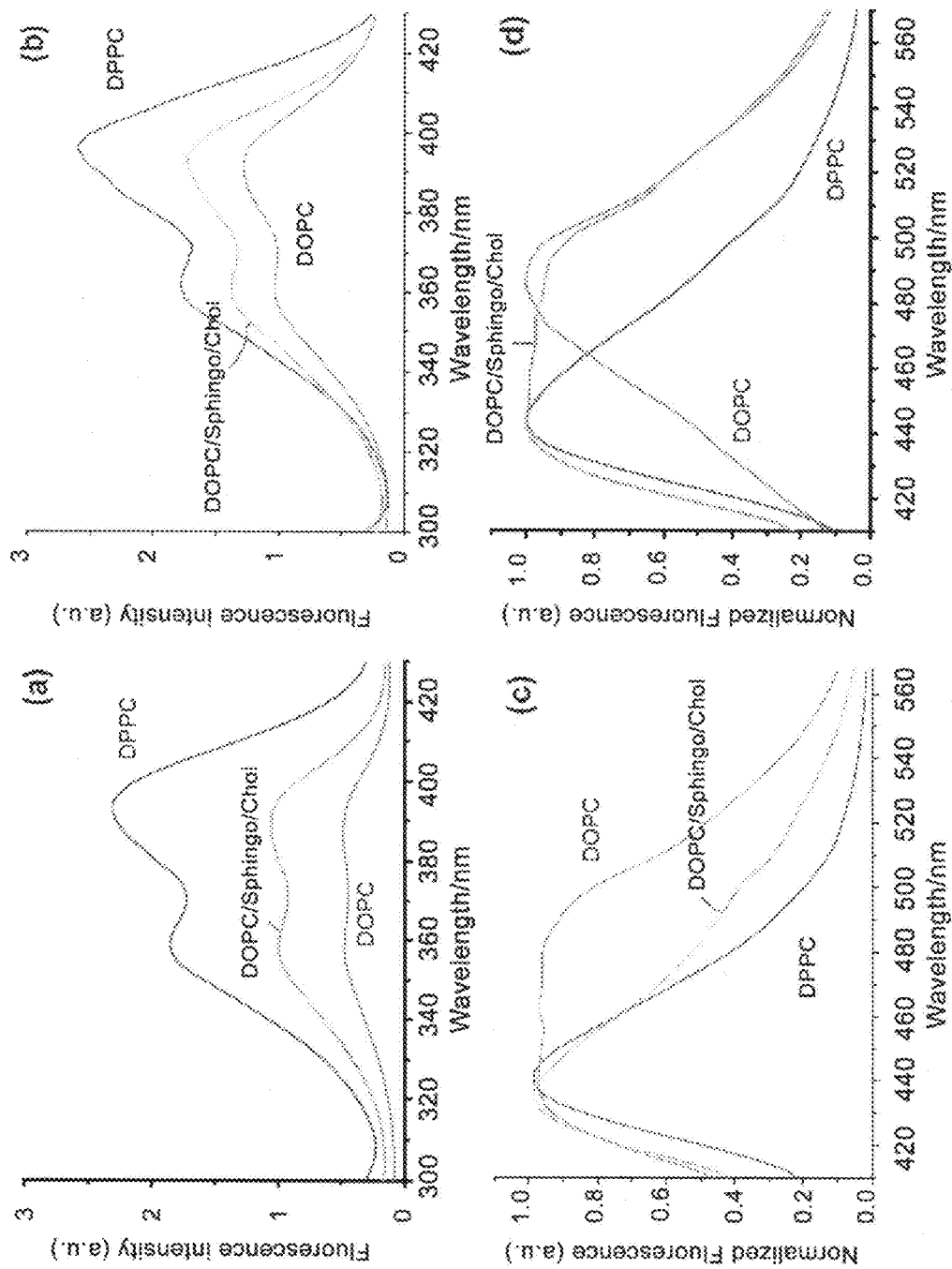
FIGS. 3a to 3d show the spectral properties of DOPC, DOPC/sphingo/chol and DPPC liposomes stained with two-photon dyes prepared in Comparative Example 1 (FIGS. 3a and 3c) and Example 1 (FIGS. 3b and 3d)

Three kinds of liposomes having different fluidity (polarity) were prepared to examine how much the two-photon dyes prepared in Example 1 and Comparative Example 1 reflected the polarity of the liposomes. Specifically, DOPC liposomes were prepared from 1,2-dioleoyl-sn-glycerol-3-phosphocholine (DOPC) having unsaturated fatty acids so as to reflect the fluidity of phospholipids of plasma membranes. The DOPC liposomes were relatively fluid. DOPC/Sphingo/Chol liposomes were composed of DOPC, sphingomyelin and cholesterol in the same ratio so as to simultaneously reflect phospholipids and lipid rafts. DPPC liposomes were prepared from 1,2-dipalmitoyl-sn-glycerol-3-phosphocholine (DPPC) so as to reflect lipid rafts. The DPPC liposomes were in a gel state and had lowest fluidity. Next, the three kinds of liposomes were stained with Laurdan and TPD1, and their spectral properties were examined. The results are shown in FIG. 3. Referring to FIGS. 3a (Laurdan) and 3b (TPD1), the maximum one-photon absorption wavelengths of Laurdan and TPD1 were in the range of 360-395 nm, regardless of the kind of the liposomes. However, the fluorescence intensity of the liposomes increased with the hydrophobicity of the liposomes in the order: DOPC<DOPC/Sphingo/Chol<DPPC. In all cases, the fluorescence intensity values of TPD1 were about 2-5 times stronger than those of Laurdan, indicating that the one-photon fluorescence of TPD1 is more efficient than Laurdan. Since the two-photon allowed states of dipolar molecules are predicted to be similar to the Franck-Condon states, this result is consistent with the fact that the two-photon absorption of TPD1 at 780 nm is more efficient than Laurdan. Normalized fluorescence spectra for Laurdan prepared in Comparative Example 1 are shown in FIG. 3c. Referring to FIG. 3c, the maximum fluorescence wavelength of Laurdan in DPPC is 440 nm and the fluorescence spectrum of

TABLE 1

| Solvent | $\lambda_{max}$ | | $\lambda^{fl}_{max}$ | | $\lambda^{(2)}_{max}$ | | $\Phi$ | | $\delta_{max}$ (GM) | |
|---|---|---|---|---|---|---|---|---|---|---|
| | Ex. 1 | Comp. Ex. 1 | Ex. 1 | Comp. Ex. 1 | Ex. 1 | Comp. Ex. 1 | Ex. 1 | Comp. Ex. 1 | Ex. 1 | Comp. Ex. 1 |
| Hexane | 345 | 344 | 404 | 407 | — | — | 0.10 | 0.11 | — | — |
| DMF | 363 | 356 | 446 | 454 | 780 | 780 | 0.36 | 1.00 | 167 | 50 |
| Ethanol | 383 | 363 | 494 | 487 | 780 | 780 | 0.43 | 1.00 | 153 | 57 |
| Water | 384 | 354 | 522 | 431 | 820 | — | 0.11 | 0.01 | 323 | — |

Laurdan in DOPC is broader. Two peaks were observed at 439 nm and 484 nm, implying that domains highly soluble in the DOPC liposomes and insoluble aggregates coexist in Laurdan.

In the meanwhile, the fluorescence wavelength bands of Laurdan in DOPC/Sphingo/Chol and DPPC were confirmed to overlap almost completely. This overlapping indicates that Laurdan was preferentially bound to rigid domains (gel) rather than to fluid domains (sol) in the DOPC/Sphingo/Chol liposomes, in which phospholipids were mixed with lipid rafts, making it difficult to discriminate the two domains by imaging. In contrast, TPD1 prepared in Example 1 emitted fluorescence of 442 nm in DPPC and fluorescence of 486 nm in DOPC (FIG. 3d). In addition, the fluorescence spectrum of TPD1 in the DOPC/Sphingo/Chol liposomes is broad and almost the same as the sum of the spectra in the DPPC and DOPC liposomes. This indicates that the two-photon dye molecules of the present invention were homogeneously distributed in rigid membrane domains and fluid membrane domains of the liposomes, in which phospholipids were mixed with lipid rafts. Therefore, since the two-photon dye of the present invention is uniformly distributed, irrespective of the difference in polarity (fluidity) within cell membranes, and emits fluorescence of different wavelength bands depending on the difference in polarity (fluidity), the polarity (fluidity) of the cell membranes can be clearly discerned, which demonstrates that the two-photon dye of the present invention is suitable for use in real-time imaging of lipid rafts.

Figure 4:
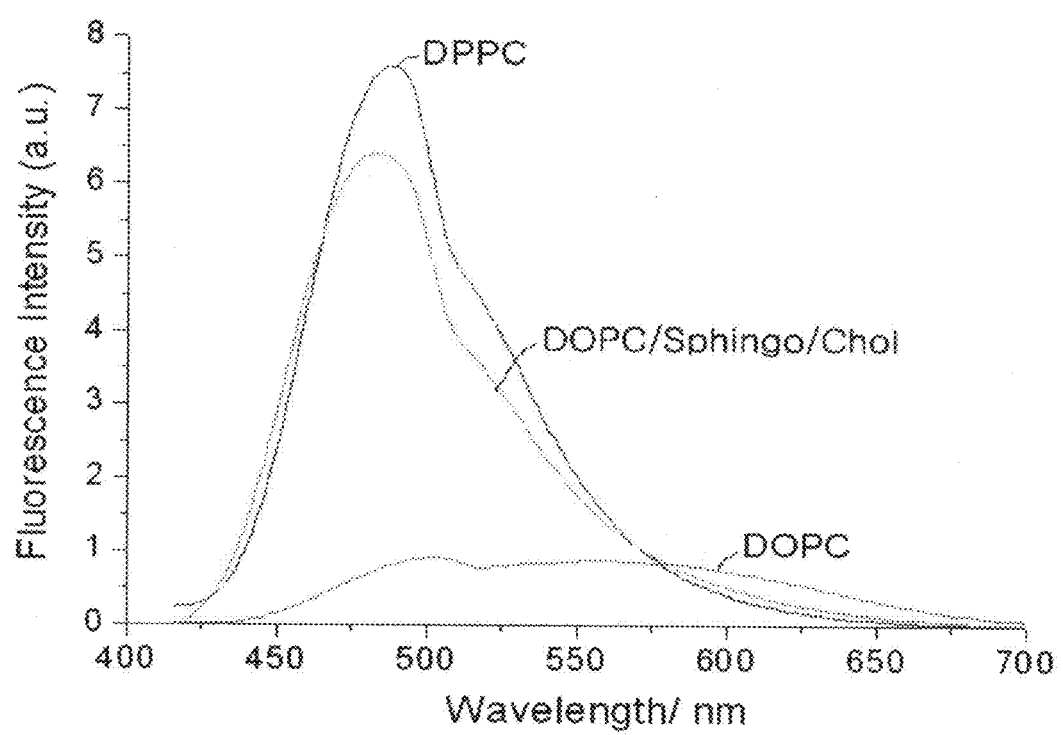
FIG. 4 is a graph showing fluorescence spectra of DOPC, DOPC/sphingo/chol and DPPC liposomes stained with a two-photon dye prepared in Example 4.

On the other hand, the different kinds of liposomes were stained with TPD4 prepared in Example 4, and their fluorescence spectra were examined. The results are shown in FIG. 4. Referring to FIG. 4, the fluorescence intensity of the fluid DOPC liposomes (in a hydrophilic environment) was 1/8 of that of the DPPC liposomes and about 1/6.5 of that of the DOPC/Sphingo/Chol liposomes. These results lead to the conclusion that the two-photon dye prepared in Example 4 can be used to clearly discriminate the hydrophobic environment (rigid membranes) from the hydrophilic environment (fluid membranes) due to the difference in fluorescence intensity.

Test Example 4

Photoselection Tests in Giant Unilamellar Vesicles (GUVs)

Figure 5:
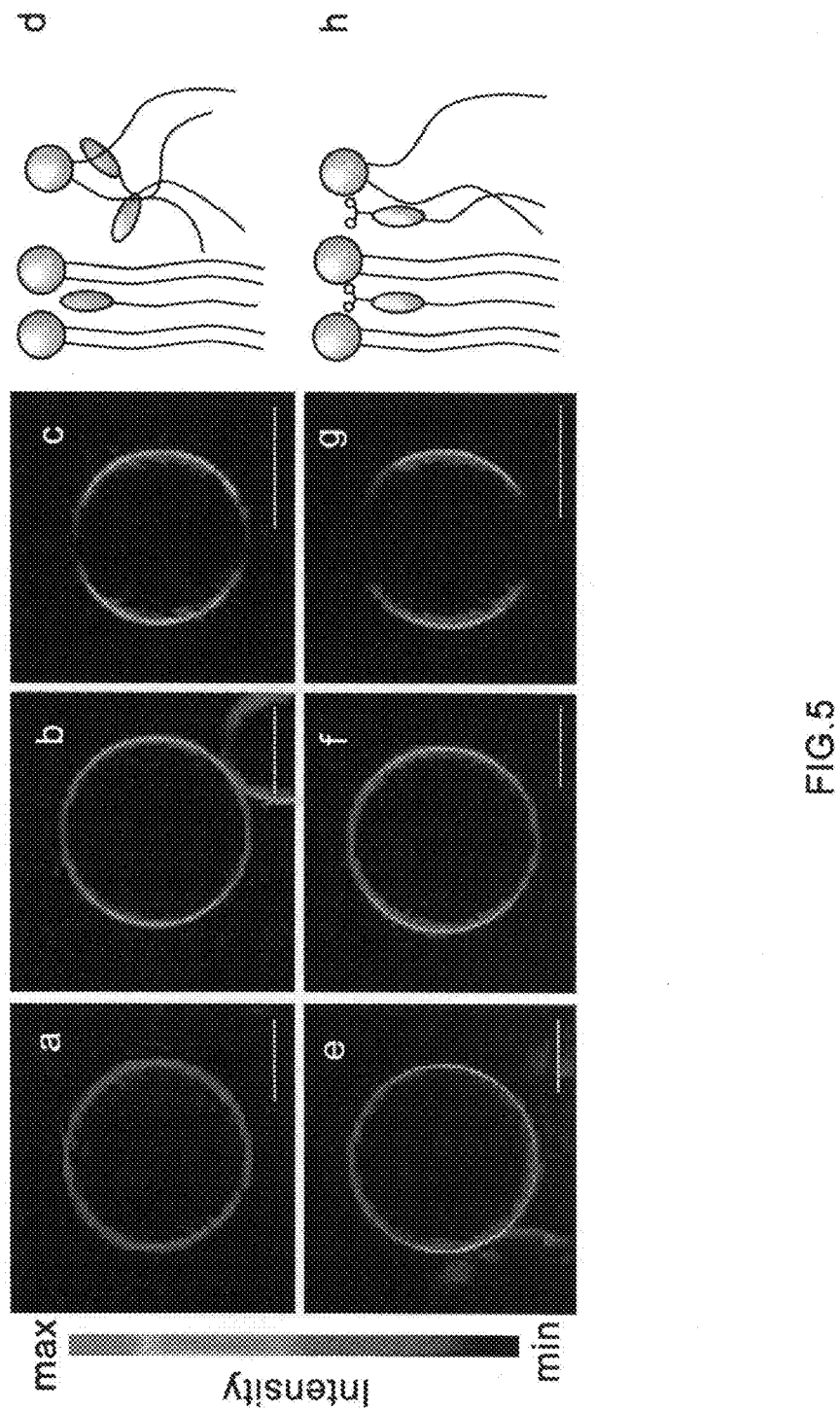
FIGS. 5a, 5b, 5c, 5e, 5f and 5g show fluorescence emitted from DOPC giant unilamellar vesicles (GUVs) (FIGS. 5a and 5e), DOPC/Sphingo/Chol GUVs (FIGS. 5b and 5f) and DPPC GUVs (FIGS. 5c and 5g) stained with two-photon dyes prepared in Example 1 and Comparative Example 1 by polarization.
FIGS. 5d and 5h schematically show the locations of the two-photon dyes prepared in Comparative Example 1 (FIG. 5d) and Example 1 (FIG. 5h) in the lipid bilayers.

Two-photon fluorescence depending on the angle of polarize light provides information about the relative orientation of the two-photon markers present in lipid bilayers. Giant unilamellar vesicles (GUVs) composed of DOPO, DOPC/Sphingo/Chol and DPPC were prepared and stained with Laurdan prepared in Comparative Example 1 and TPD1 prepared in Example 1. The distributions of fluorescence emitted from the stained GUVs by polarization were examined. The results are shown in FIGS. 5a, 5b, 5c, 5e, 5f and 5g. FIGS. 5a, 5b and 5c are photographs showing the distributions of fluorescence emitted from the DOPC GUVs, DOPC/Sphingo/Chol GUVs and DPPC GUVs stained with Laurdan prepared in Comparative Example 1, respectively. FIGS. 5e, 5f and 5g are photographs showing the distributions of fluorescence emitted from the DOPC GUVs, DOPC/Sphingo/Chol GUVs and DPPC GUVs stained with TPD1 prepared in Example 1, respectively. These photographs reveal that the Laurdan- or TPD1-stained DOPC/Sphingo/Chol GUVs and DPPC GUVs showed very low fluorescence intensity in areas perpendicular to the polarization. The fluorescence emitted from the Laurdan-stained DOPC GUVs was uniform but weak in all areas (FIG. 5a), which indicates that Laurdan molecules were randomly oriented in the DOPC GUVs. In contrast, the fluorescence emitted from the TPD1-stained DOPC GUVs was very weak in areas perpendicular to the polarization but was strong in the other areas (FIG. 5e). These observations show that the TPD1 molecules were located parallel to the fatty acid tails even in the DOPC GUVs. In addition, the two-photon dye of the present invention was confirmed to be photoselective even in the DOPC GUVs and homogeneously stain the DOPC GUVs. FIGS. 5d and 5h are schematic diagrams illustrating the locations of the two-photon markers present in the lipid bilayers. In the gel phase (i.e. rigid state), both Laurdan and TPD1 were located parallel to the lipid molecules. In the fluid phase, however, Laurdan molecules were randomly oriented or existed as aggregates. In contrast, the TPD1 molecules were located parallel to the lipid molecules probably because of the favorable hydrophilic interactions between the water molecules and the carboxylates near the lipid head groups.

Test Example 5

Reflection Tests of Hydrophilicity and Hydrophobicity of Giant Unilamellar Vesicles Using Generalized Polarization (GP) Images A GP image is obtained using a fluorescent dye by the following procedure. First, cells or model membranes are stained with a fluorescent dye. The intensities of fluorescence emitted from the stained cells or model membranes are measured at 400-460 nm and 470-530 nm. A GP value is calculated by Equation 2:

$$GP = \frac{I_{(400-460)} - G \times I_{(470-530)}}{I_{(400-460)} + G \times I_{(470-530)}} \quad (2)$$

wherein $I_{(400-460)}$ represents the fluorescence intensity at a wavelength of 400 to 460 nm, $I_{(470-530)}$ represents the fluorescence intensity at a wavelength of 470 to 530 nm, and G is the sensitive correction factor in the two wavelength ranges.

The cells or model membranes are colored depending on the obtained GP value to obtain a final GP image.

As the GP value approximates −1, the cells or model membranes are in a hydrophilic environment, which is colored violet or blue. As the GP value approximates 1, the cells or model membranes are in a hydrophobic environment, which is colored red or orange.

Figure 6:
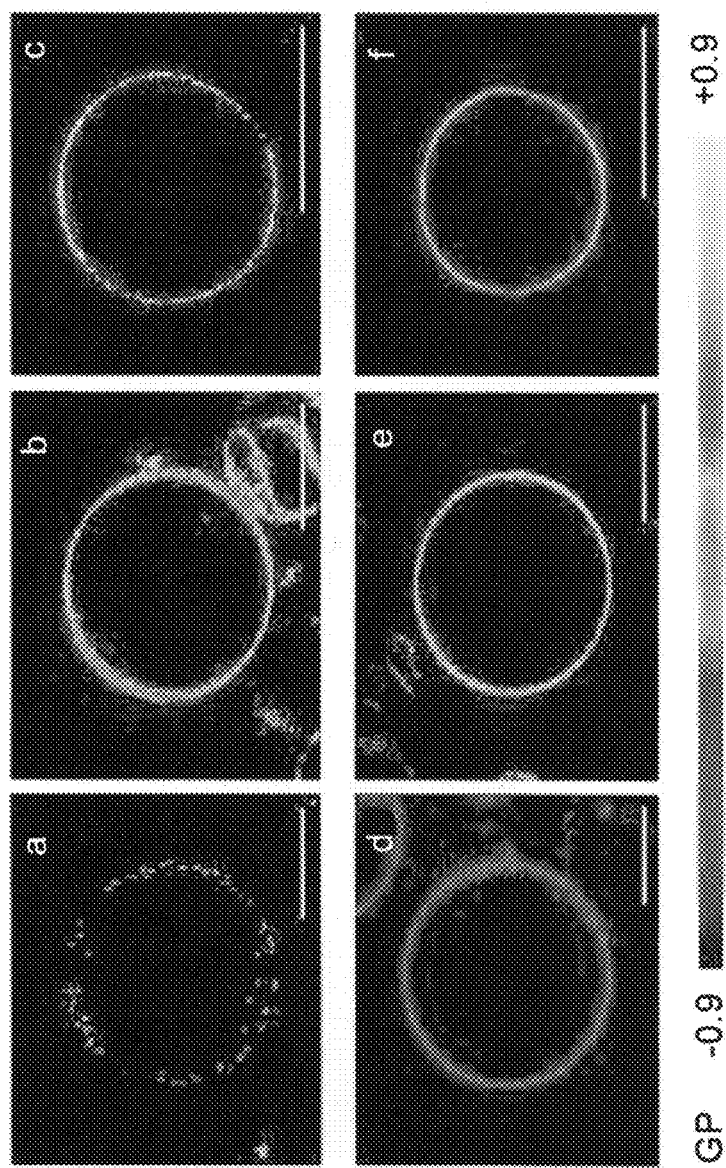
FIGS. 6a through 6c show two-photon fluorescence generalized polarization (GP) images of DOPC GUVs, DOPC/Sphingo/Chol GUVs and DPPC GUVs stained with a two-photon dye prepared in Comparative Example 1, respectively
FIGS. 6d through 6f are two-photon fluorescence generalized polarization (GP) images of DOPC GUVs, DOPC/Sphingio/Chol GUVs and DPPC GUVs stained with a two-photon dye prepared in Example 1.
Figure 7:
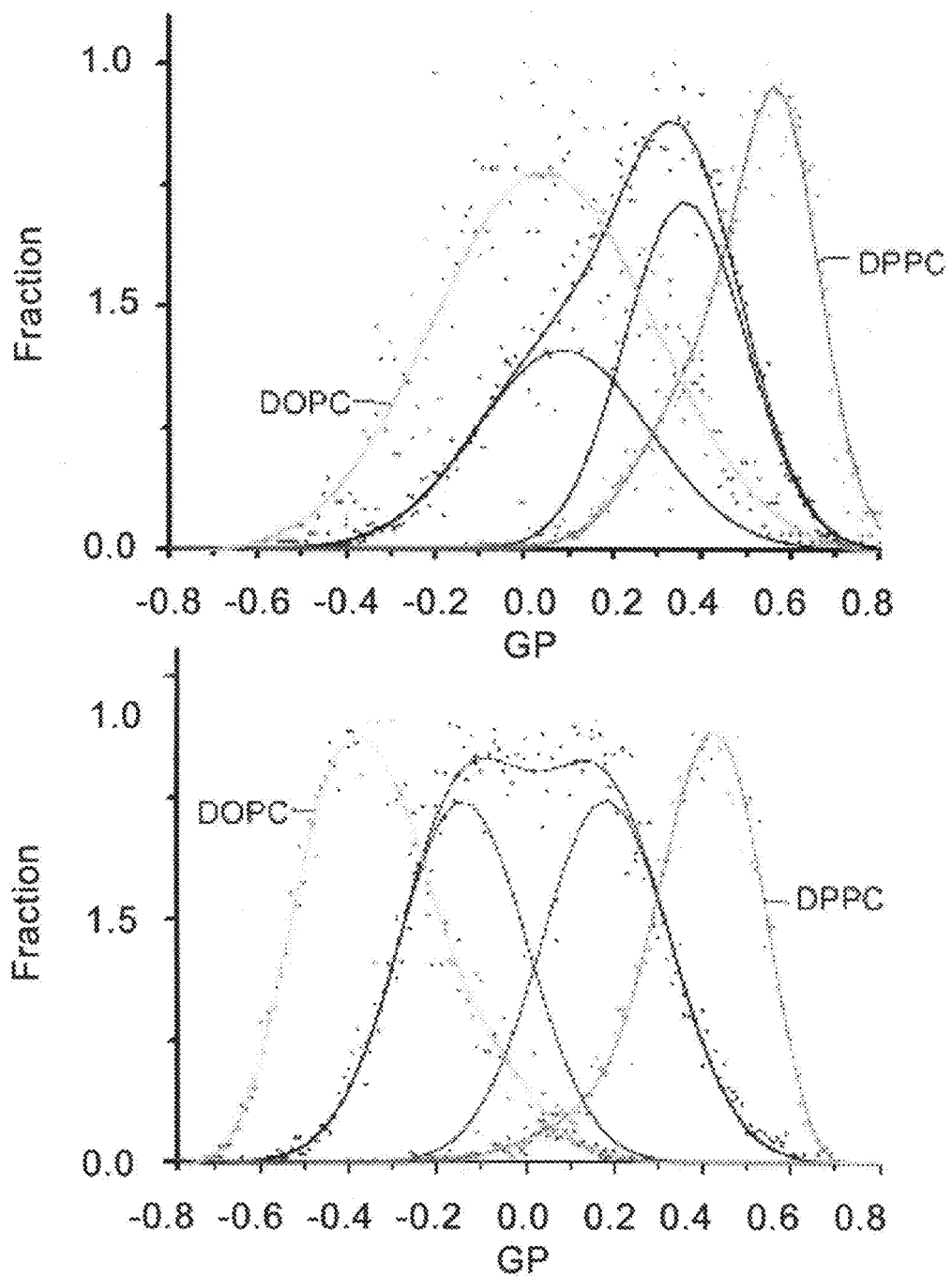
FIG. 7 shows two-photon fluorescence GP distribution curves of DOPO GUVs, DOPC/Sphingo/Chol GUVs and DPPC GUVs stained with two-photon dyes prepared in Comparative Example 1 (upper) and Example 1 (lower)

The three kinds of GUVs were stained with Laurdan prepared in Comparative Example 1 and TPD1 prepared in Example 1. GP values were calculated in the equatorial sections of the GUVs and converted into images. The images are shown in FIGS. 6a through 6f. Specifically, FIG. 6a through 6c are fluorescence GP images of the DOPC GUVs, DOPC/Sphingo/Chol GUVs and DPPC GUVs stained with Laurdan prepared in Comparative Example 1, respectively, and FIG. 6d through 6f are fluorescence GP images of the DOPC GUVs, DOPC/Sphingo/Chol GUVs and DPPC GUVs stained with TPD1 prepared in Example 1, respectively. FIG. 7 shows GP distribution curves for Laurdan and TPD1 (blue: DOPC GUVs, red: DPPC GUVs, black: DOPC/Sphingo/Chol GUVs). Referring to FIG. 7, the GP distribution curves for the DPPC GUVs are narrow and the center GP values are 0.54 for Laurdan and 0.41 for TPD1, respectively. The center GP values in the DOPC GUVs are 0.044 for Laurdan and −0.35 for TPD1, respectively. The center GP values in the DOPC GUVs are generally negative because the DOPC GUVs is highly hydrophilic. However, the reason why the center GP value for Laurdan is positive is because Laurdan probably aggregated in the fluid membranes. In contrast, since TPD1 did not aggregate, the center GP value in the DOPC GUVs is negative, which demonstrates that the DOPC GUVs were in a hydrophilic environment. These results show that TPD1 can be used to more clearly discriminate the fluid membrane from the rigid membrane than Laurdan. Similar results could also be found in the GP distribution curves of the DOPC/sphingo/chol GUVs. Specifically, the GP values in the GUVs stained with Laurdan were slightly higher and the GP distribution curves of the GUVs stained with TPD1 were more symmetrical. When the respective distribution curves were converted into bimodal distribution curves by Gaussian Curve Fitting, the center GP values were 0.09 and 0.36 for the Laurdan-stained GUVs and −0.14 and 0.18 for the TPD1-stained GUVs, respectively. The two peaks for the TPD1-stained GUVs are symmetrical with respect to about zero and the respective GP values are substantially symmetrical. The center GP values are significantly larger for Laurdan than TPD1. Also, the low GP distribution curve is much broader than the high one. These results indicate that Laurdan was exposed to various environments with different polarity and existed as aggregates in fluid environment. However, both the widths and shapes of the low and high GP distribution curves for the TPD1-stained GUVs are very similar and symmetrical, indicating that TPD1 can better reflect and more clearly discriminate the environments of the rigid (hydrophobic) membrane and the fluid (hydrophilic) membrane in the GUVs.

In the present invention, one- and two-photon fluorescence images were obtained using spectral confocal multiphoton microscopes (TCS SP2, Leica). An argon laser (488 nm) was used as the excitation source for one-photon fluorescence microscopy, and a mode-locked titanium-sapphire laser (780 nm) was used as the excitation source for two-photon fluorescence microscopy. Calculation of the GP values was performed using a home-made program based on the visual C++ format.

Test Example 6

GP Imaging Tests in Cells

Figure 8:
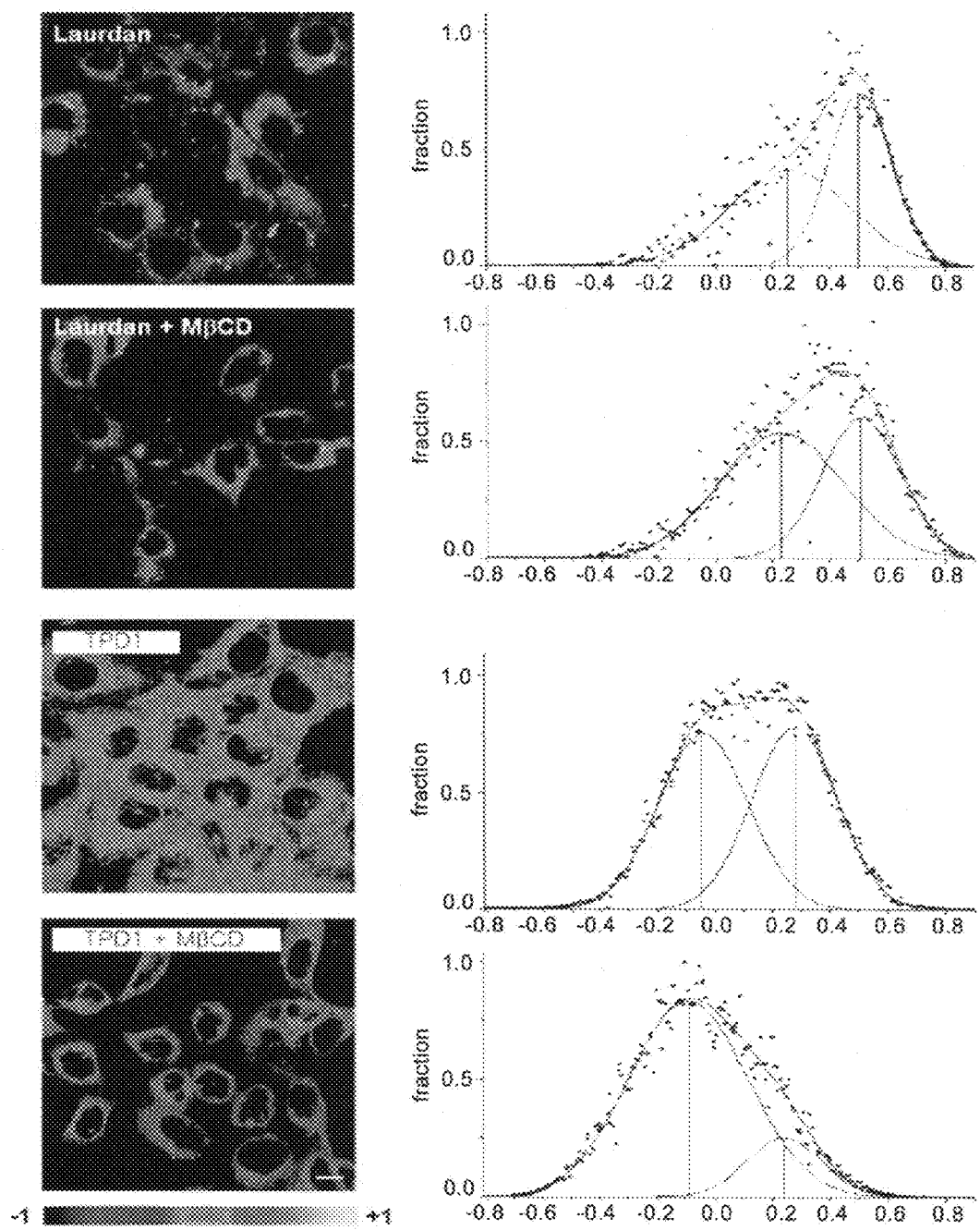
FIG. 8 shows GP images and GP distribution curves of intact A431 cells and MβCD-treated A431 cells stained with two-photon dyes prepared in Example 1 and Comparative Example 1.

Intact A431 cells and A431 cells treated with methyl-β-cyclodextrin (MβCD), a drug removing cholesterol from plasma membranes, as samples were prepared. The intact A431 cells and the samples were stained with the two-photon dyes prepared in Example 1 and Comparative Example 1, and their images were obtained by two-photon fluorescence microscopy. The respective images were converted into GP images and the GP distribution curves were plotted. The GP images and distribution curves are shown in FIG. 8. MβCD is known to destroy lipid rafts of cell membranes by removing cholesterol. In principle, the peak in the low GP distribution curve representing hydrophilicity should be unaltered while the peak in the high GP distribution curve representing hydrophobicity should disappear upon treatment of the cell membranes with MβCD. The graphs of FIG. 8 show that after the Laurdan-stained cells were treated with MβCD, the peak (center GP value=0.49) in the high GP distribution curve did not disappear and the center GP value was slightly shifted to 0.51. This result may lead to the false conclusion that lipid rafts still exist in cholesterol-free cells. In contrast, the images of the TPD1-stained cells are brighter and more uniform than those of the Laurdan-stained cells. The peak in the high GP distribution curve did not completely disappear, but its size was markedly decreased. Referring to the GP images of the Laurdan-stained cells, the hydrophobic domains (lipid rafts) are not clearly discriminated from the hydrophilic domains (phospholipids). Referring to the GP images of the MβCD-treated cells, since some areas disappeared ambiguously and randomly, it is impossible to discern which areas were lipid rafts in the image obtained before treatment with MβCD. In contrast, the two-photon dye of the present invention can be used to clearly discriminate between the hydrophobic and hydrophilic domains of the cell membranes and image the two domains. The hydrophobic domains (lipid rafts) are visualized by red fluorescence, and the hydrophilic domains (phospholipids) are visualized by blue fluorescence. The two domains are clearly discernible. From the image obtained after treatment with MβCD, it can be confirmed that the domains (lipid rafts) visualized by red fluorescence before treatment with MβCD completely disappeared. Therefore, the two-photon dye of the present invention can be used to satisfactorily image real lipid raft domains.

Test Example 7

Cytotoxicity Tests

Figure 9:
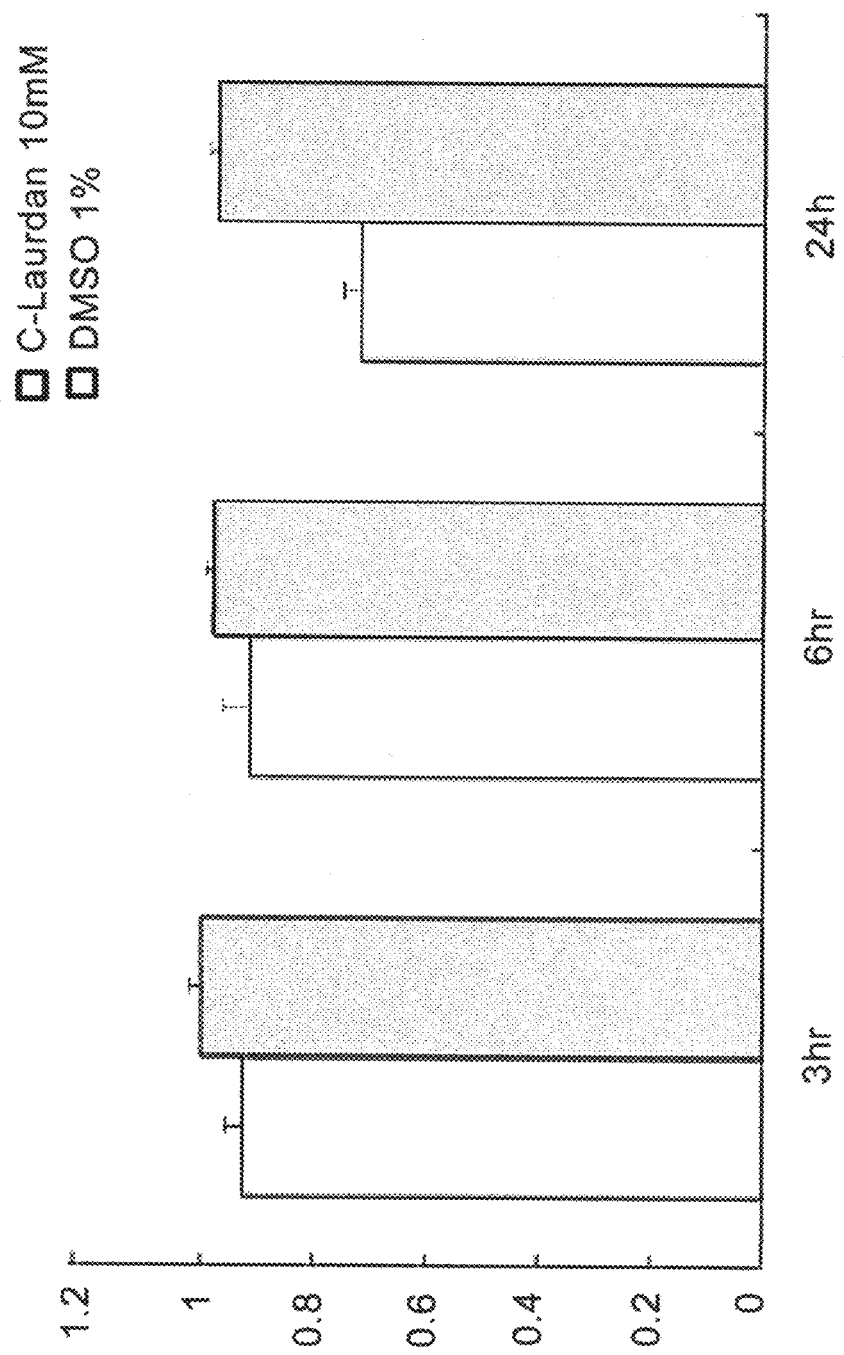
FIG. 9 shows the results of MTT assay for a two-photon dye prepared in Example 1.

To evaluate whether the two-photon dyes of the present invention are cytotoxic or not, MTT assay was done on the two-photon dye prepared in Example 1. Specifically, A431 cells were stained with TPD1 ($1 \times 10^{-5}$ M) and DMSO (1%) was used as a reference solvent. The results are shown in FIG. 9. Referring to FIG. 9, the y-axis shows cell viability. There was no significant difference in cytotoxicity between TPD1 and the reference solvent after incubation for 6 hours. Therefore, it can be concluded that the two-photon dye of the present invention is suitable for imaging of living cells.

Test Example 8

Fluorescence GP Imaging of Living Cells

Figure 10:
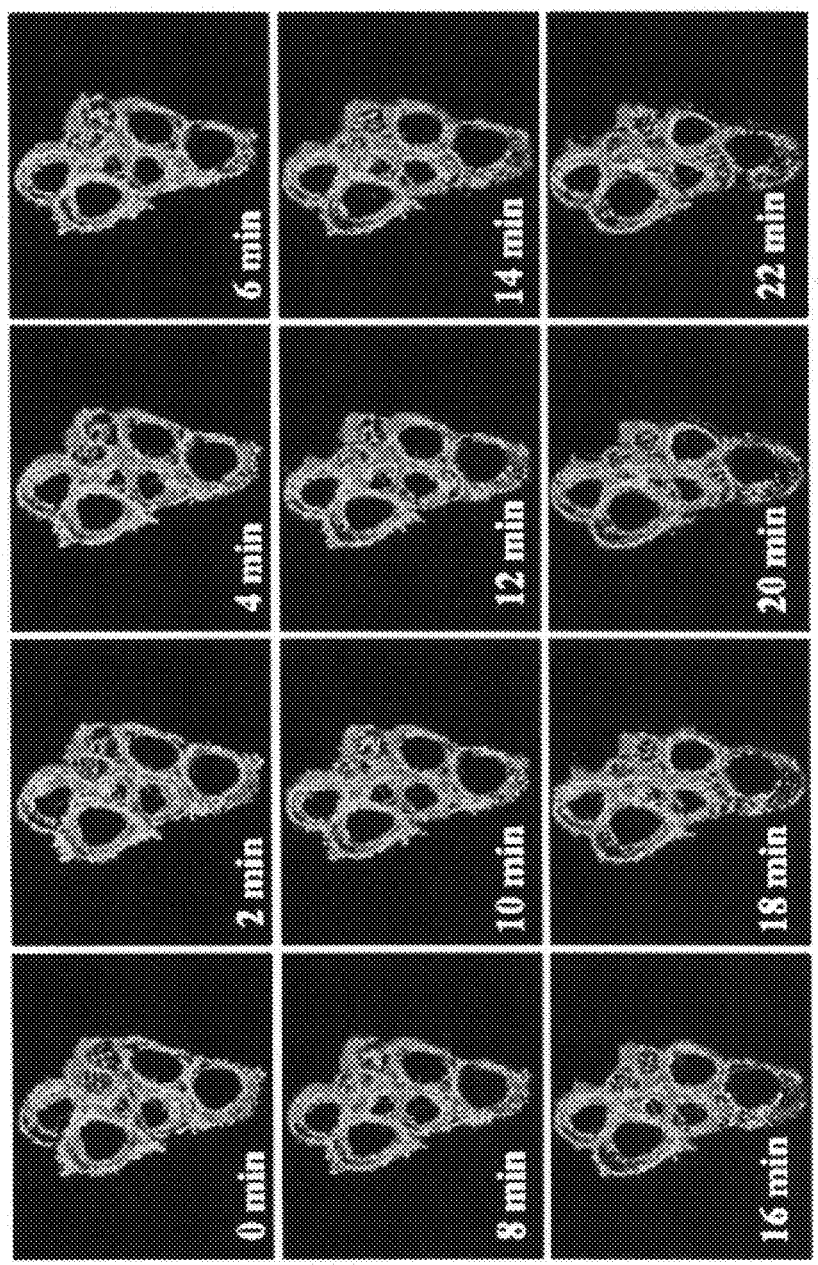
FIG. 10 shows time-dependent images of A431 cells stained with a two-photon dye prepared in Example 1.

A431 cells stained with TPD1 ($1 \times 10^{-5}$ M), which was prepared in Example 1, were subjected to fluorescence GP imaging for 22 minutes. The images thus obtained are shown in FIG. 10. The images of FIG. 10 indicate that the two-photon dye of the present invention is very useful in visualizing lipid rafts over a long period of time. In addition, the images confirm that the lipid rafts (designated by red domains) of the cells did not remain stationary but dynamically moved.

Test Example 9

Direct Fluorescence Imaging

Figure 11:
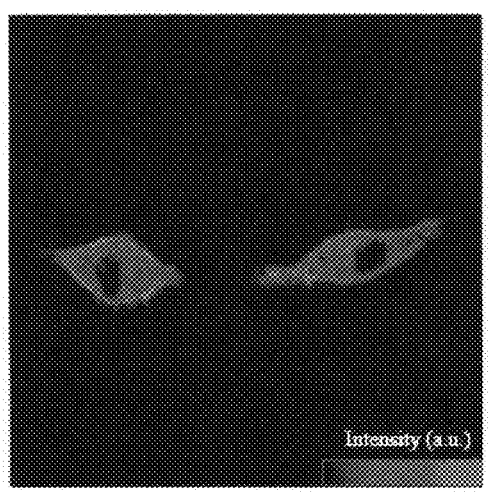
FIGS. 11*a* and 11*b* show direct one-photon and two-photon fluorescence images of macrophage cells co-stained with a dye prepared in Example 4 and BODIPY-G$_{M1}$.
FIG. 11*c* is an overlapped image of the fluorescence images shown in FIGS. 11*a* and 11*b*.
Figure 11:
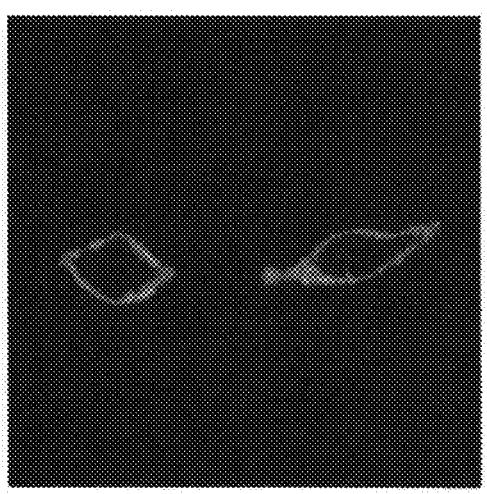
Figure 11:
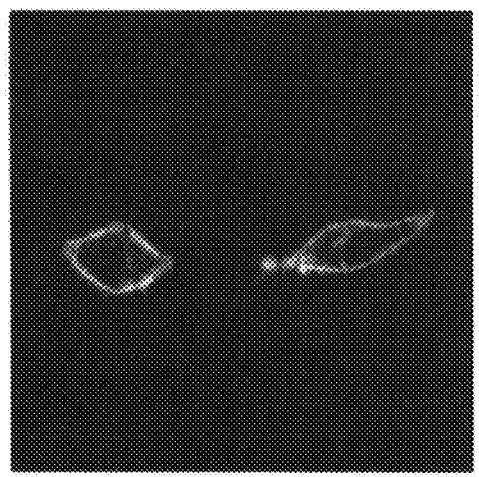

After macrophage cells were co-stained with the dye (TPD4, $1 \times 10^{-5}$ M) prepared in Example 4 and a one-photon dye (BODIPY-$G_{M1}$, $1 \times 10^{-5}$ M) commonly used in the art, direct one-photon and two-photon fluorescence images of the macrophage cells were obtained. The images are shown in FIGS. 11a and 11b. Specifically, FIG. 11a is a two-photon fluorescence image of the macrophage cells stained with the two fluorescent dyes, and FIG. 11b is a one-photon fluorescence image of the same cells at an excitation wavelength of 488 nm (TPD4 can also be one-photon excited at an excitation wavelength around 400 nm, but is not excited at a wavelength of 488 nm. Accordingly, TPD4 does not emit one-photon fluorescence). FIG. 11c is an overlapped image of the two fluorescence images. This test was conducted to identify whether the bright (red colored) domains in the two-photon fluorescence image of TPD4 correspond to actual lipid raft domains. Referring to FIG. 11c, the domains judged to be lipid rafts by one-photon fluorescence of BODIPY-$G_{M1}$ almost completely overlap the bright domains in the fluorescence image of TPD4. These observations demonstrate that TPD4 of the present invention can be used to clearly visualize actual lipid raft domains and directly observe lipid rafts.

As apparent from the foregoing, the two-photon dyes of the present invention emit fluorescence with high intensity in the environments of cell membranes and can be used to clearly discriminate the hydrophobic and hydrophilic domains of the cell membranes. Therefore, the use of the two-photon dyes according to the present invention enables satisfactory imaging of actual lipid raft domains. In addition, since the two-photon dyes of the present invention show no cytotoxicity, they can be suitably used in bioimaging applications, for example, real-time imaging of lipid rafts over a long period of time.

What is claimed is:

1. A two-photon dye for real-time imaging of lipid rafts, represented by Formula 1:

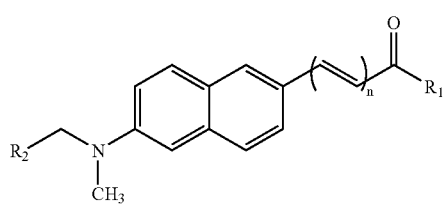
(1)

wherein $R_1$ is a $C_5$-$C_{17}$ alkyl group,
n is 0 or 1, and
$R_2$ is —COOH, —$CH_2SO_3Na$ or

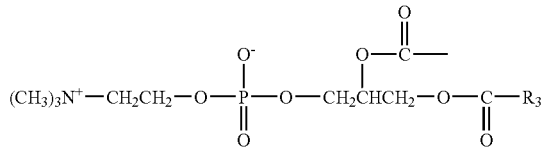

($R_3$ is a $C_5$-$C_{17}$ alkyl group).

2. The two-photon dye according to claim 1, wherein the compound of Formula 1 is selected from the group consisting of the following compounds (2):

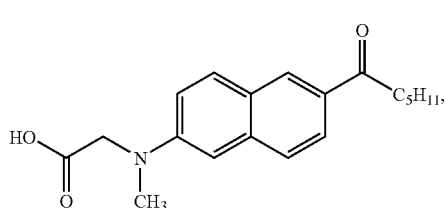
(2)

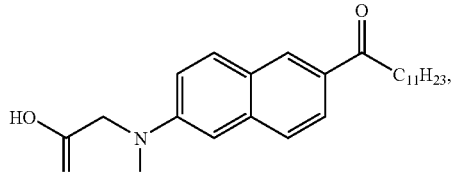

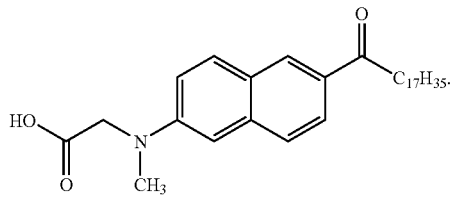

3. The two-photon dye according to claim 1, wherein the compound of Formula 1 is the compound represented by Formula 3:

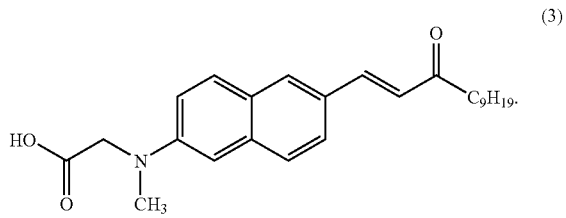
(3)

4. The two-photon dye according to claim 1, wherein the compound of Formula 1 is selected from the group consisting of the following compounds (4):

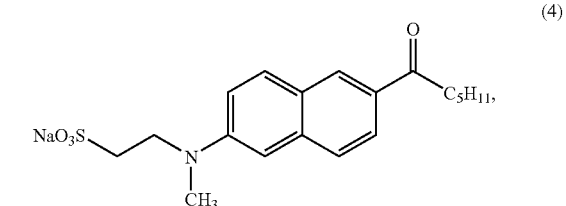
(4)

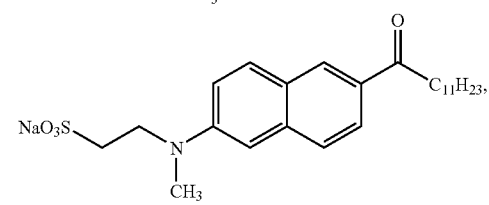

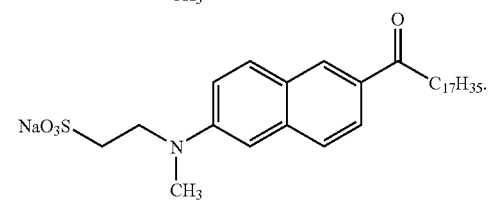

5. The two-photon dye according to claim 1, wherein the compound of Formula 1 is selected from the group consisting of the following compounds (5):

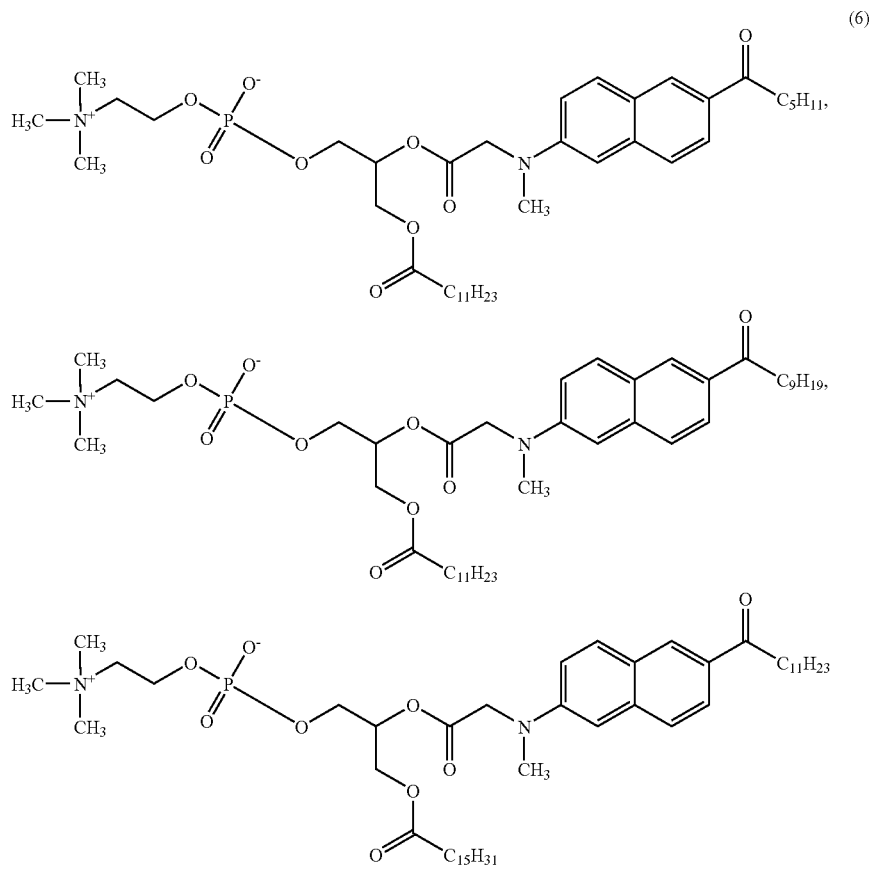

(6)

6. The two-photon dye according to claim 1, wherein the two-photon dye has a two-photon absorption efficiency not lower than 20 GM in living cells, is two-photon excited by a light source at 750-1,000 nm, and emits fluorescence ranging from 400 to 700 nm.

7. The two-photon dye according to claim 1, wherein the two-photon dye has a two-photon absorption efficiency not lower than 150 GM, and emits fluorescence of 430-470 nm in a hydrophobic environment and fluorescence of 470-530 nm in a hydrophilic environment.

* * * * *